(12) United States Patent
Koller (10) Patent No.: US 11,173,006 B2
(45) Date of Patent: Nov. 16, 2021

(54) MEDICAL CIRCULATION DETENT DEVICE, MEDICAL INSTRUMENT AND MEDICAL STERILIZATION CONTAINER

(71) Applicant: Aesculap AG, Tuttlingen (DE)

(72) Inventor: Tobias Koller, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 749 days.

(21) Appl. No.: 15/989,369

(22) Filed: May 25, 2018

(65) Prior Publication Data

US 2018/0271611 A1 Sep. 27, 2018

Related U.S. Application Data

(63) Continuation of application No. PCT/EP2016/079708, filed on Dec. 5, 2016.

(30) Foreign Application Priority Data

Dec. 8, 2015 (DE) .......................... 102015121322.2

(51) Int. Cl.
*A61L 2/00* (2006.01)
*A61B 50/30* (2016.01)
(Continued)

(52) U.S. Cl.
CPC ................ *A61B 50/30* (2016.02); *A61L 2/07* (2013.01); *A61L 2/26* (2013.01);
(Continued)

(58) Field of Classification Search
CPC ..... A61J 1/00; A61J 2200/40; A61B 17/2833; A61B 17/29; A61B 2017/2946;
(Continued)

(56) References Cited

U.S. PATENT DOCUMENTS 2,024,004 A  12/1935 Jewell et al.
2,613,130 A  10/1952 Jewell et al.
(Continued)

FOREIGN PATENT DOCUMENTS

CN  1498119  5/2004
CN  1582247  2/2005
(Continued)

OTHER PUBLICATIONS

European Patent Office English Translation of the description and the claims sections for DE 102009034992 A1.*

*Primary Examiner* — Monzer R Chorbaji
(74) *Attorney, Agent, or Firm* — Lipsitz & McAllister, LLC (57) ABSTRACT

The invention relates to a medical circulation detent device, comprising at least one circulation body and a latching element. The at least one circulation body comprising a restricted guide and at least one latching receptacle for the latching element. The latching element is guidable through the restricted guide from an unlatched position to a latched position at a first side of the at least one latching receptacle into the latter, and at a second side of the at least one latching receptacle from the latched position to an unlatched position again. An operative element is coupled to the latching element via a coupling element. A thermal actuating element is operatively connected to the latching element and transferable due to temperature from a first state to a second state and vice versa in order to move the operative element. The invention also relates to a medical sterilization container.

19 Claims, 4 Drawing Sheets

(51) Int. Cl.
  *A61L 2/26* (2006.01)
  *A61L 2/07* (2006.01)
  *A61B 90/00* (2016.01)
  *A61B 17/00* (2006.01)
  *A61B 50/00* (2016.01)

(52) U.S. Cl.
  CPC ............. *A61B 2017/00867* (2013.01); *A61B 2017/00871* (2013.01); *A61B 2050/005* (2016.02); *A61B 2050/0074* (2016.02); *A61B 2090/0803* (2016.02); *A61B 2090/0813* (2016.02); *A61L 2202/122* (2013.01)

(58) Field of Classification Search
  CPC .... A61B 2017/305; A61B 2017/00867; A61B 2050/0067; A61B 2050/0075; A61B 2050/0076; A61L 2202/182
  USPC .................................................. 422/297, 300
  See application file for complete search history.

(56) References Cited

U.S. PATENT DOCUMENTS

| | | | |
|---|---|---|---|
| 2,715,251 A | 8/1955 | Vischer, Jr. | |
| 3,034,819 A | 5/1962 | Tupper | |
| 3,484,036 A | 12/1969 | Meyers | |
| 3,924,800 A | 12/1975 | Desmond et al. | |
| 3,972,416 A | 8/1976 | Underwood | |
| 4,372,921 A | 2/1983 | Sanderson et al. | |
| 4,416,417 A | 11/1983 | Sanderson et al. | |
| 4,457,327 A * | 7/1984 | Pepper .................... | A61L 2/26 137/67 |
| 4,509,196 A | 4/1985 | Sak et al. | |
| 4,512,498 A | 4/1985 | Leibinger | |
| 4,551,311 A | 11/1985 | Lorenz | |
| 4,562,047 A | 12/1985 | Sestak et al. | |
| 4,625,885 A | 12/1986 | Nichols | |
| 4,661,326 A | 4/1987 | Schainholz | |
| 4,682,688 A | 7/1987 | Budert | |
| 4,782,942 A | 11/1988 | Ashley et al. | |
| 4,783,321 A | 11/1988 | Spence | |
| 4,820,499 A | 4/1989 | Taschner | |
| 4,915,913 A | 4/1990 | Williams et al. | |
| 5,147,351 A | 9/1992 | Wagner | |
| 5,176,884 A | 1/1993 | Taschner et al. | |
| 5,225,162 A | 7/1993 | Scoville | |
| 5,328,661 A | 7/1994 | Taschner | |
| 5,346,075 A | 9/1994 | Nichols et al. | |
| 5,382,528 A | 1/1995 | Scoville | |
| 5,508,006 A | 4/1996 | Gabele et al. | |
| 5,524,755 A | 6/1996 | Deeds | |
| 5,690,713 A | 11/1997 | Bowerman et al. | |
| 6,053,914 A | 4/2000 | Eggers et al. | |
| 6,077,485 A | 6/2000 | Baker | |
| 6,145,687 A | 11/2000 | Nichols et al. | |
| 6,295,330 B1 | 9/2001 | Skog et al. | |
| 7,172,740 B2 | 2/2007 | Gleichauf et al. | |
| 7,744,832 B2 | 6/2010 | Horacek et al. | |
| 9,393,077 B2 | 7/2016 | Schuster | |
| 10,363,331 B2 | 7/2019 | Schulz et al. | |
| 2004/0256269 A1 | 12/2004 | Gleichauf et al. | |
| 2004/0262189 A1 | 12/2004 | Fraser et al. | |
| 2007/0163911 A1 | 7/2007 | Gelardi | |
| 2008/0125624 A1 | 5/2008 | Hatori | |
| 2008/0187465 A1 | 8/2008 | Horacek et al. | |
| 2012/0156096 A1 | 6/2012 | Allen et al. | |
| 2016/0263264 A1 | 9/2016 | Schulz et al. | |

FOREIGN PATENT DOCUMENTS

| | | | |
|---|---|---|---|
| CN | 1899211 | 1/2007 | |
| CN | 101287657 | 10/2008 | |
| CN | 201275152 | 7/2009 | |
| CN | 103889362 | 6/2014 | |
| DE | 747432 | 9/1944 | |
| DE | 8213351 | 8/1982 | |
| DE | 3116036 | 11/1982 | |
| DE | 3202430 | 7/1983 | |
| DE | 3316141 | 11/1984 | |
| DE | 3438463 | 4/1986 | |
| DE | 3500026 | 7/1986 | |
| DE | 3544341 | 6/1987 | |
| DE | 3632674 | 4/1988 | |
| DE | 19835503 | 2/2000 | |
| DE | 20118910 | 3/2002 | |
| DE | 10314072 | 10/2004 | |
| DE | 202009010210 | 11/2009 | |
| DE | 102009034992 | 2/2011 | |
| DE | 102009034992 A1 * | 2/2011 | ... A61B 2017/00867 |
| DE | 102013111979 | 4/2015 | |
| EP | 0281255 | 9/1988 | |
| EP | 0412571 | 2/1991 | |
| JP | 5441591 | 4/1979 | |
| JP | 57170258 | 10/1982 | |
| JP | 03222956 | 10/1991 | |
| JP | 2000185047 | 7/2000 | |
| JP | 2006180935 | 7/2006 | |
| JP | 2010516425 | 5/2010 | |
| WO | 7900077 | 2/1979 | |
| WO | 9206899 | 4/1992 | |
| WO | 0051648 | 9/2000 | |
| WO | 2015062924 | 5/2015 | |

* cited by examiner

MEDICAL CIRCULATION DETENT DEVICE, MEDICAL INSTRUMENT AND MEDICAL STERILIZATION CONTAINER

CROSS REFERENCE TO RELATED APPLICATIONS

The present application is a continuation patent application of international application number PCT/EP2016/079708, filed on Dec. 5, 2016 and claims the priority of German patent application No. DE 10 2015 121 322.2, filed on Dec. 8, 2015, which are incorporated herein by reference in their entirety and for all purposes.

FIELD OF THE INVENTION

The present invention relates to a medical circulation detent device, comprising at least one circulation body and a latching element, the at least one circulation body comprising a restricted guide and at least one latching receptacle for the latching element, and the latching element being guidable through the restricted guide from an unlatched position to a latched position at a first side of the at least one latching receptacle into the latter, and at a second side of the at least one latching receptacle from the latched position to an unlatched position again.

The present disclosure further relates to a medical instrument, comprising a medical circulation detent device.

The invention further relates to a medical sterilization container, comprising a circulation detent device.

BACKGROUND OF THE INVENTION

A circulation detent device of the kind mentioned at the outset is used, for example, in a surgical instrument which comprises two parts movable relative to each other, one of which comprises the latching element and the other the at least one circulation body. The parts can be moved relative to each other, and the latching element is thereby guided into the latching receptacle. Upon further movement of the parts relative to each other in the same direction, the latching element unlatches from the latching receptacle, and the parts can be moved in the opposite direction relative to each other. During this procedure, the latching element runs through the restricted guide and is transferred from an unlatched position first into the latched position and subsequently into an unlatched position again. Such an instrument is described in DE 103 14 072 A1, for example. In the case of the circulation detent of this instrument, provision is made, as also in other surgical instruments, for the parts to be moved relative to each other by a user.

An object underlying the present invention is to provide a generic medical circulation detent device which enables the movement of two parts relative to each other without intervention by the user.

SUMMARY OF THE INVENTION

In a first aspect of the invention, a medical circulation detent device comprises at least one circulation body and a latching element, the at least one circulation body comprising a restricted guide and at least one latching receptacle for the latching element, and the latching element being guidable through the restricted guide from an unlatched position to a latched position at a first side of the at least one latching receptacle into the latter, and at a second side of the at least one latching receptacle from the latched position to an unlatched position again. The circulation detent device comprises an operative element coupled to the latching element via a coupling element, and a thermal actuating element operatively connected to the latching element and transferable due to temperature from a first state to a second state and vice versa in order to move the operative element, the first state and the second state comprising a low-temperature state and a high-temperature state and also a state of lesser extent and a state of greater extent. In order to transfer the latching element from the unlatched position to the latched position in the at least one latching receptacle and in order to transfer the latching element from the latched position to an unlatched position, the actuating element is respectively transferable from the first state to the second state and to the first state again, and the latching element is thereby movable in the restricted guide.

In a second aspect of the invention, a medical instrument comprises at least one circulation detent device in accordance with the first aspect. The medical instrument is, in particular, a medical sterilization container.

BRIEF DESCRIPTION OF THE DRAWINGS

The foregoing summary and the following description may be better understood in conjunction with the drawing figures. There are shown in.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical circulation detent device, comprising at least one circulation body and a latching element, the at least one circulation body comprising a restricted guide and at least one latching receptacle for the latching element, and the latching element being guidable through the restricted guide from an unlatched position to a latched position at a first side of the at least one latching receptacle into the latter, and at a second side of the at least one latching receptacle from the latched position to an unlatched position again. The circulation detent device comprises an operative element coupled to the latching element via a coupling element, and a thermal actuating element operatively connected to the latching element and transferable due to temperature from a first state to a second state and vice versa in order to move the operative element, the first state and the second state comprising a low-temperature state and a high-temperature state and also a state of lesser extent and a state of greater extent. In order to transfer the latching element from the unlatched position to the latched position in the at least one latching receptacle and in order to transfer the latching element from the latched position to an unlatched position, the actuating element is respectively transferable from the first state to the second state and to the first state again, and the latching element is thereby movable in the restricted guide.

The present invention incorporates the concept that owing to movement of the latching element in the restricted guide, an operative element coupled to the latching element can also be moved. For this purpose, the circulation detent device comprises the coupling element. For movement of the latching element through the restricted guide, a thermal actuating element operatively connected to the latching element is provided. The actuating element can be transferred from a first state to a second state and vice versa in a thermally induced manner. Provision is made for the actuating element to assume a low-temperature state and a high-temperature state. This makes it possible for the actuating element to change between the low-temperature state and the high-temperature state and vice versa owing to a change in temperature. The first and the second states further comprise a state of greater extent and a state of lesser extent. In dependence upon the respective state, the actuating element may, for this reason, be of different extent, and a movement, due to temperature, of the latching element operatively connected to the actuating element can thereby be initiated. In this way, the circulation detent device can, for example, be used on a medical instrument whose operative element (first part) is to be moved upon a change in temperature on the instrument (second part), with the operative element being able to assume different positions after two opposite changes in temperature—heating and cooling or cooling and heating. This is achieved by the latching element being able to be transferred from the unlatched position to the latched position and first held therein. The operative element can thereby be moved from an original position to a second position and held therein. To move the operative element back into the original position again, the circulation detent device can again be subjected to two opposite changes in temperature—heating and cooling or cooling and heating—so that the latching element is transferred from the latched position out of the latching receptacle into an unlatched position again.

The circulation detent device may preferably be comprised by a medical sterilization container with a valve device, with the operative element forming the valve body of the valve device. This makes it possible, in particular, starting from a closed state, to implement an open state and a closed state again of the valve device only after at least two successive heating and cooling phases.

It may be provided that the first state is the low-temperature state and the second state the high-temperature state. The latching element can be moved from the unlatched position to the latched position by heating and cooling and from the latched position to the unlatched position by repeated heating and cooling.

Alternatively, it may be provided that the first state is the high-temperature state and the second state the low-temperature state. The latching element can be moved from the unlatched position to the latched position by cooling and heating and from the latched position to the unlatched position by repeated cooling and heating.

Furthermore, provision may be made for the first state to be the state of lesser extent and the second state the state of greater extent. The actuating element can be provided with a greater extent by transferring the actuating element from the first to the second state. The extent of the latching element can be reduced by transfer from the second to the first state. It may be provided that in order to move the latching element in the latter case a setting element comprised by the circulation detent device is operatively connected to the latching element. For example, the setting element engages the coupling element in order to move the latching element to the latched position or to the unlatched position again.

Alternatively, provision may be made for the first state to be the state of greater extent and the second state the state of lesser extent. Here it may be provided that when transferring the actuating element from the first state to the second state with reduction of its extent, a setting element is operatively connected to the latching element in order to move it. For example, the setting element engages the coupling element. When transferring the actuating element from the second state to the first state and thereby increasing the extent of the actuating element, the actuating element can move the latching element to the latched position or to the unlatched position again.

In an advantageous embodiment of the circulation detent device, the first state is the low-temperature state of lesser extent of the actuating element, and the second state the high-temperature state of greater extent of the actuating element.

It proves advantageous for the actuating element to consist of or comprise a phase transformation material, which assumes different phases in the first state and the second state. The phase transformation material can be a phase change material such as, for example, a latent heat storage material, or the shape memory material mentioned hereinbelow.

The actuating element preferably consists of or comprises a shape memory material.

The shape memory material is advantageously a two-way shape memory material. The actuating element may have in both the high-temperature state and the low-temperature state different, intrinsic shapes, in which the actuating element has extents of different size. The actuating element can be transferred by a change in temperature from the one to the respective other shape, in order to change the extent.

The shape memory material is preferably a shape memory metal. In the present case, "shape memory metal" includes an alloy of metals.

For example, the shape memory metal is nitinol, other metal alloys also being conceivable.

The shape memory material may, for example, also be a shape memory polymer.

The actuating element may be configured as spring element, for example, as pressure spring or alternatively as tension spring.

For example, the actuating element is helical and surrounds the coupling element and/or the operative element.

It proves expedient for the circulation detent device to comprise a setting element which is operatively connected to the latching element and moves it when the actuating element is transferred from the state of greater extent to the state of lesser extent. If the actuating element is transferred from the state of lesser to the state of greater extent, it can work to move the latching element. The stetting element can work in a corresponding manner on the latching element when the actuating element is transferred from the state of greater to the state of lesser extent.

The setting element may be configured as spring element, which may, for example, be a pressure spring. Alternatively, it is conceivable for the setting element to be configured as tension spring. The spring element can be helical and surround the coupling element.

It is advantageous for the circulation detent device to comprise or form at least one stop element, which is fixed to the coupling element, for the actuating element and/or for the stetting element. A force of the actuating element and/or of the setting element for moving the coupling element and thereby the latching element can act on the stop element. The stop element is, in particular, a stop which is movable relative to an instrument comprising the circulation detent device. The actuating element and/or the setting element can be supported on the at least one stop element.

Expediently, a common stop element is provided, with the actuating element and the setting element acting with forces in opposite directions on the stop element.

For example, the actuating element and the setting element are arranged on opposite sides of the stop element.

It is advantageous for the circulation detent device to comprise or form at least one stop element for the actuating element, which at least one stop element is fixed or fixable to an instrument comprising the circulation detent device. As a result, the stop element can, in particular, be stationary on the instrument and absorb a force (for example, by the actuating element being supported on the stop element), the counteracting force of which is exerted by the actuating element on the aforementioned stop element in order to move the coupling element.

It is expedient for the circulation detent device to comprise or form at least one stop element for the setting element, which at least one stop element is fixed or fixable to an instrument comprising the circulation detent device. As a result, the stop element can, in particular, be stationary in relation to the instrument and absorb a counteracting force to that force (for example, by the setting element being supported on the stop element), which is exerted by the setting element on the first aforementioned stop element.

The at least one circulation body can comprise a bearing element for rotatable and/or displaceable mounting on an instrument comprising the circulation detent device.

The coupling element can comprise at least one bearing element for displaceable and/or rotatable mounting on an instrument comprising the circulation detent device.

The operative element can be or comprise a valve body of a valve device. This is, for example, the valve device of a medical sterilization container.

The latching element can be rigidly coupled to the operative element via the coupling element.

The coupling element is expediently formed in one piece with the latching element and/or with the operative element.

The coupling element may be rod-shaped.

The restricted guide is, for example, a link guide.

The at least one latching receptacle is, for example, formed as latching recess on the least one circulation body.

In an advantageous embodiment of the circulation detent device, the restricted guide comprises a ramp for the latching element, over which the latter slides during transfer from the unlatched position to the latched position, and the restricted guide comprises a stop member which holds the latching element back after the sliding-over, and on which a control surface guiding the latching element into the latching receptacle is arranged. The latching element can be moved over the ramp in the restricted guide when the actuating element is transferred from the first to the second state. When the actuating element is transferred from the second to the first state, the latching element can be held back by the stop member and guided via the control surface into the latched position in the latching receptacle.

The restricted guide preferably comprises an entrance channel, forming the ramp, for the latching element, so as to enable reliable guidance of the latching element.

A control surface for the latching element can be arranged at the entrance channel in order to guide it into the entrance channel. It may be provided that for this purpose the circulation body is moved and, in particular, pivoted at the bearing element relative to the instrument when the latching element contacts the control surface.

The restricted guide expediently comprises a control surface which the latching element contacts during transfer from the latched position to the unlatched position, in order to move and, in particular, to pivot the at least one circulation body at a bearing element relative to the instrument. The latching element can be moved by transfer of the actuating element from the first to the second state and contact the control surface. This allows, for example, the circulation body to be moved, in particular, pivoted at the bearing element. For example, the latching element is thereby transferred into an exit channel of the restricted guide.

Accordingly, the restricted guide may comprise an exit channel for the latching element, at the start of which the control surface is arranged.

The restricted guide can comprise a ramp, for example, at the exit channel. It may be provided that during transfer from the latched position to the unlatched position, the latching element slides over the ramp, with the restricted guide comprising a stop member which holds the latching element back after the sliding-over, in order to avoid entrance into the restricted guide in the opposite, "wrong" direction.

It may be provided that the at least one circulation body comprises precisely one latching receptacle, starting from which the latching element is transferable to the unlatched position. For example, for this purpose, the latching element is transferred from the latched position back into the unlatched position under the action of the setting element.

In a different advantageous embodiment of the circulation detent device, it may be provided that the at least one circulation body comprises at least one further latching receptacle for the latching element, in which the latter can assume a further latched position, the actuating element being transferable from the second state to the first state and to the second state again, and the latching element thereby being movable in the restricted guide, in order to transfer the latching element from the latched position to the further latched position. This makes it possible, for example, for the operative element to be moved back into the starting position again only after three cycles of a change in temperature (heating and cooling or cooling and heating three times) and in the meantime latching of the latching element in the latching receptacle twice.

In accordance with the aforementioned embodiment, it may also be provided that the circulation body comprises more than two latching receptacles for the latching element, and starting from one latching receptacle, the latching element can be transferred to the next latching receptacle, in each case, by transferring the actuating element from the first to the second state and vice versa.

An advantageous embodiment of the circulation detent device can comprise a plurality of circulation bodies fixed or formed on a common holding part, a respective exit of a restricted guide of a circulation body opening into or being adjacent to a respective entrance of a restricted guide of an adjacent circulation body. The circulation bodies are, for example, held on a holding part rotatable on the instrument and are radially aligned in relation to a bearing element which defines the axis of rotation.

The last aforementioned advantageous embodiment is, in particular, of advantage when the circulation detent device comprises a counter which is operatively connected to the holding part and counts a respective circulation of the latching element on the circulation bodies. This allows, for example, cycles of changes in temperature (heating and cooling or cooling and heating) to be counted. Here it is, for example, provided that with a number n of circulation bodies with one latching receptacle in each case, 2n cycles of changes in temperature have to be completed before the counter advances one step. The counter can be mechanically or electronically configured and have a display.

As mentioned at the outset, the present disclosure further relates to a medical instrument. An instrument in accordance with the invention comprises a circulation detent device of the aforementioned kind.

The instrument may be, in particular, a medical sterilization container.

Accordingly, the present invention also relates to a medical sterilization container. A sterilization container in accordance with the invention comprises a circulation detent device of the aforementioned kind. The sterilization container comprises a valve device with a valve opening formed in a container wall and a valve body, the valve body being the operative element of the circulation detent device.

The valve body can, for example, be moved by the actuating element due to heating from a closed position covering the valve opening and upon cooling again, with release of the valve opening, be arranged in an open position at a distance from the valve opening, with the latching element latching in the latching receptacle. Upon heating again and subsequent cooling, the valve body can be transferred from the open position at a distance from the valve opening to a closed positon again, in which the valve body closes the valve opening. In this way, the invention offers the possibility of bringing about an open state and a closed state of the valve device only after at least two successive heating and cooling procedures. If the circulation body has more than two latching receptacles, as explained hereinabove, it is also conceivable that more than two heating and cooling procedures are to be performed. With such a sterilization container, it is, for example, provided that condensate occurring during a steam sterilization process is to be discharged from the container interior via the valve opening. The circulation detent device can be used here with a valve opening of comparatively small cross section, and condensate that occurs can be safely discharged by holding the valve body in the open position after a plurality of changes in temperature.

In an expedient manner, the valve body closes the valve opening in the unlatched position of the latching element and releases it in the latched position of the latching element.

Figures 1, 2:
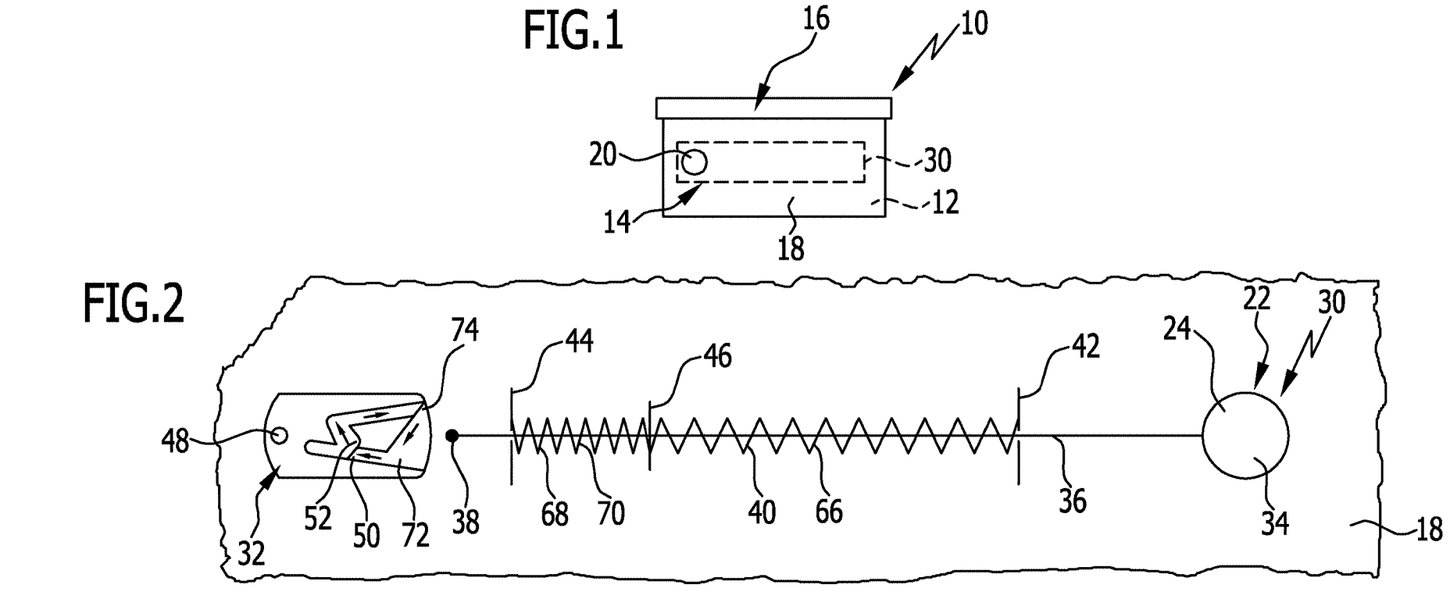
FIG. 1: schematically a medical sterilization container in accordance with the invention, comprising a medical circulation detent device in accordance with the invention.
FIG. 2: schematically the circulation detent device of the sterilization container from FIG. 1 with a latching element assuming an unlatched position and an actuating element assuming a first state.

FIG. 1 shows a preferred embodiment of a medical sterilization container in accordance with the invention, which is denoted by reference numeral 10. The sterilization container 10 is regarded, in the present case, as medical instrument.

The sterilization container 10 defines a container interior 12 in which surgical instruments to be sterilized can be positioned. The container interior 12 is formed by a sterilization container tub 14 and a sterilization container lid 16 placed thereon. The sterilization container 10 comprises a container wall designated in its entirety 18. The container wall may be a wall of the sterilization container tub 14 (for example, the bottom wall or a side wall) or a wall of the sterilization container lid 16.

A valve opening 20 is formed in the container wall 18, in the present case, by way of example, in a side wall of the sterilization container tub 14. The valve opening 20 is shown schematically in FIG. 1 and also in FIGS. 3 to 5. FIGS. 2 to 5 and 7 show a section of the container wall 18.

The valve opening 20 is a component of a valve device 22 of the sterilization container 10, which further comprises a valve body 24. The valve body 24 and, therefore, the valve device 22 can assume a closed position in which the valve body 24 sealingly closes the valve opening 20 (FIG. 2). In the closed position of the valve body 24, the sterilization container 10 is sealingly closed.

Figure 3:
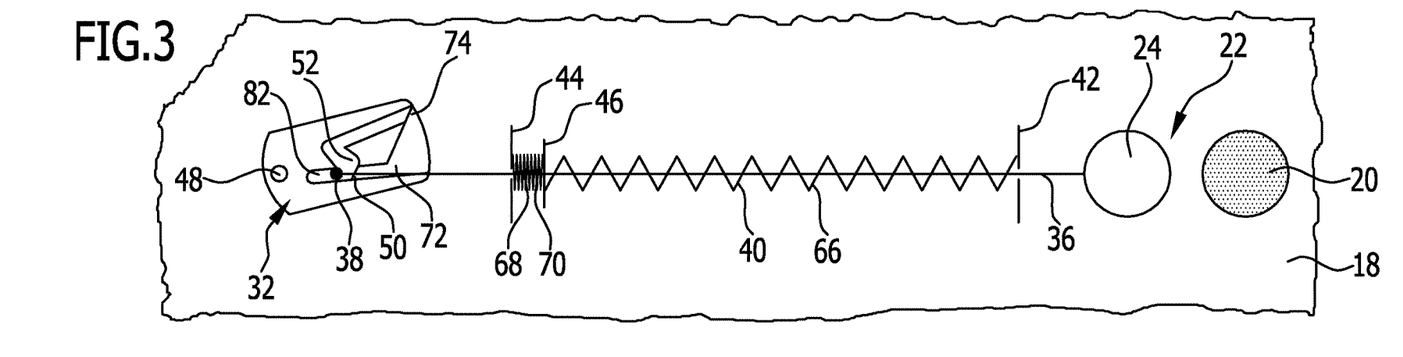
FIG. 3: a representation corresponding to FIG. 2, wherein the actuating element assumes a second state and a section of a container wall of the sterilization container is also shown.

The valve body 24 and, therefore, the valve device 22 can, furthermore, assume an open position in which the valve body 24 is lifted off a valve seat at the valve opening 20 (for example, by displacement) and is arranged at a distance from the valve opening 20. As a result, the valve opening 20 is open (FIG. 3).

During the steam sterilization of instruments, steam is introduced into the sterilization container 10, and the sterilization container 10 is subjected to changes in temperature, namely repeatedly heated and cooled in successive cycles. Condensate occurs during the sterilization and should preferably be discharged from the container interior 12 at the end of the sterilization process. For this purpose, the valve device 22 can be transferred to the open position in the manner explained hereinbelow. With the valve opening 20 open, the condensate can be discharged from the container interior 12 through the valve opening 20.

To transfer the valve body 24 to the open position and to the closed position, it must be moved relative to the valve opening 20. For this purpose, the sterilization container 10 comprises an advantageous embodiment, denoted by reference numeral 30, of a circulation detent device in accordance with the invention. FIG. 1 shows in dashed lines the contour of the circulation detent device 30, which, furthermore, is shown schematically in FIGS. 2 to 5.

Figure 6:
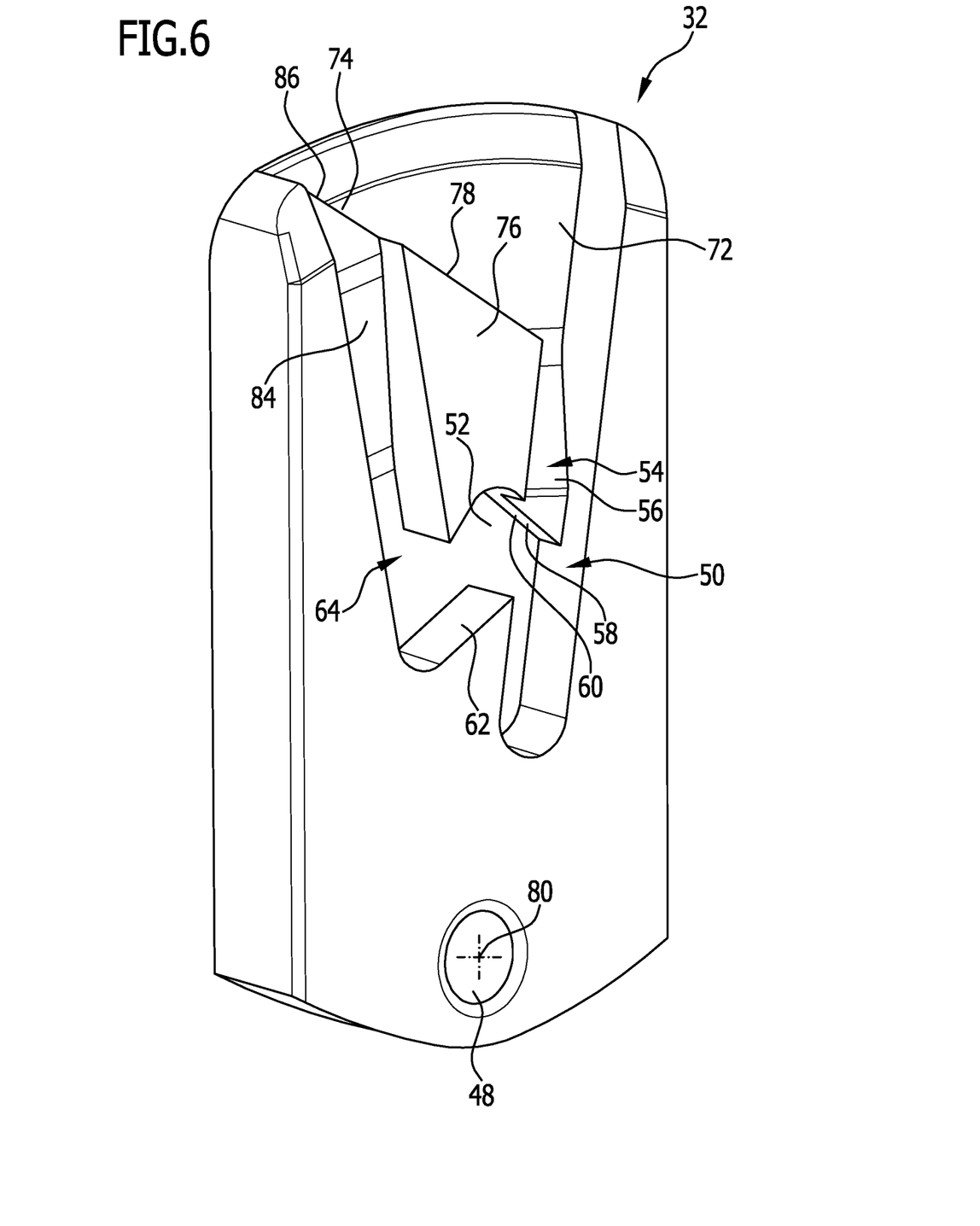
FIG. 6: a circulation body with a restricted guide for the latching element of the circulation detent device.

The circulation detent device 30 comprises a circulation body 32, which is shown separately in FIG. 6. Furthermore, the circulation detent device 30 comprises an operative element 34, in the present case, the valve body 24. The circulation detent device 30, furthermore, comprises a coupling element 36, a latching element 38, an actuating element 40, a setting element 68 and stop elements 42, 44 and 46.

The circulation body 32 comprises a bearing element 48 and a restricted guide 50 and a latching receptacle 52 for the latching element 38. The restricted guide 50 is a link guide and comprises an entrance channel 54 for the latching element 38, a ramp 56 with a stop member 58, a control surface 60, a further control surface 62 and an exit channel 64 for the latching element 38. The entrance channel 54 and the exit channel 64 are arranged on opposite sides of the latching receptacle 52.

The valve body 24 is preferably rigidly coupled to the latching element 38 via the coupling element 36. The latching element 38 and the valve body 24 are arranged on opposite sides of the coupling element 36 and are preferably connected thereto in one piece. The coupling element 36 is, in the present case, rod-shaped. The latching element 38 is, for example, a latching projection.

The coupling element 36 is movably and, in particular, slidably mounted on the container wall 18. The valve body 24 can be pushed away from the valve opening 20 and pushed towards it by sliding displacement of the coupling element 36 on the container wall 18.

The stop elements 42 and 44 are fixed to the container wall 18. As a result, both stop elements 42, 44 are stationary in relation to the sterilization container 10 comprising the circulation detent device 30. In the present case, the coupling element 36 passes through the stop elements 42 and 44. The valve body 24 and the latching element 38 are positioned on sides facing away from each other of the stop element 42, on the one hand, and of the stop element 44, on the other hand.

The stop element 46 is fixed to the coupling element 36 and, for example, connected in one piece thereto. As a result, the stop element 46 is movable relative to the container wall 18 and, in particular, movable on the sterilization container 10 comprising the circulation detent device 30. Conversely, the valve body 24 and the latching element 38 can be slidingly displaced by a movement of the stop element 46. The stop element 46 is arranged between the stop elements 42 and 44.

The actuating element 40 is positioned between the stop element 42 and the stop element 46. The actuating element 40 is, in the present case, thermally actuatable and configured as spring element 66, in particular, as pressure spring. Other configurations are, of course, conceivable.

The actuating element 40 surrounds the coupling element 36 and can be supported with a first side on the stop element 42 and with a second side on the stop element 46.

The actuating element 40 is made of a phase transformation material, which, in the present case, is a shape memory material. The shape memory material is, in particular, a two-way shape memory material. A shape memory metal, preferably, nitinol (nickel-titanium alloy) is used as shape memory material.

Figure 4:
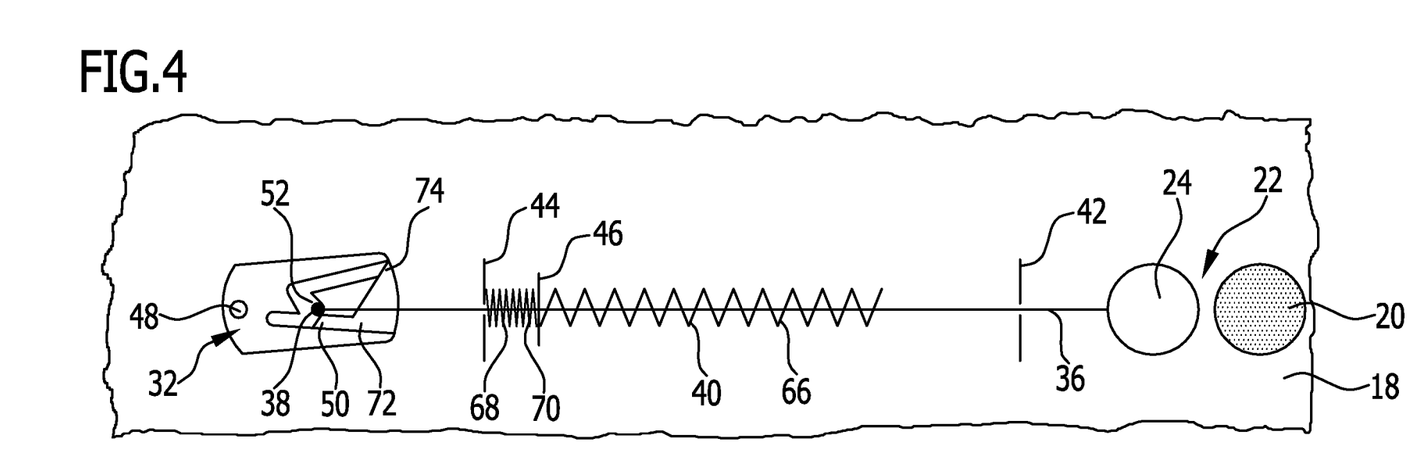
FIG. 4: a representation corresponding to FIG. 2, wherein the latching element assumes a latched position and the actuating element a first state.

Owing to the two-way shape memory material, the actuating element 40 can assume in two different states various shapes which are intrinsic in each case. In a first state, a low-temperature state, the actuating element 40 has a state of lesser extent. FIGS. 2 and 4 show the actuating element 40 in the low-temperature state, the state of lesser extent.

Figure 5:
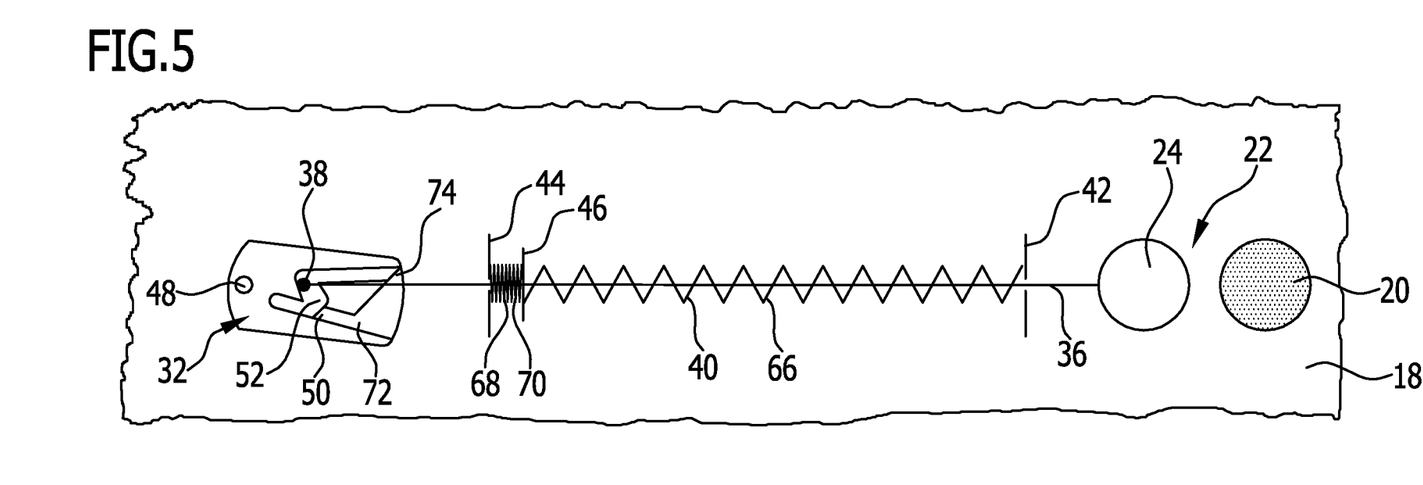
FIG. 5: a representation corresponding to FIG. 2, wherein the actuating element assumes a second state.

The actuating element 40 can be transferred to a second state by an increase in temperature. The second state is a high-temperature state in which the actuating element 40 has a state of greater extent. FIGS. 3 and 5 show the actuating element 40 in the high-temperature state, the state of greater extent.

In the low-temperature state, the extent of the actuating element 40 is less than in the high-temperature state. Independently of the state, the actuating element 40 is helical.

The actuating element 40 can be transferred from the low-temperature state to the high-temperature state by heating and thereby increased in its extent. Conversely, the actuating element 40 can be transferred from the high-temperature state by cooling to the low-temperature state and thereby decreased in its extent. The low-temperature state and the high-temperature state are assumed by different phases of the nitinol phase transformation material.

The setting element 68 of the circulation detent device 30 is arranged between the stop element 44 and the stop element 46. The setting element 68 is configured as spring element 70, in particular, as helical spring. The spring element 70 surrounds the coupling element 36. The setting element 68 can be supported with a first side on the stop element 44 and with a second side on the stop element 46.

Forces directed by the actuating element 40, on the one hand, and by the setting element 68, on the other hand, at the stop element 46 are opposite to each other. Accordingly, the setting element 68 is also a pressure spring.

The setting element 68 is, in the present case, a resetting element for moving the coupling element 36 and, therefore, the latching element 38 when the actuating element 40 is transferred from the high-temperature state to the low-temperature state.

The circulation body 32 has a first side facing the coupling element 36 and a second side facing away from the coupling element 36. Arranged at the first side is an entrance 72 of the restricted guide 50 via which the latching element 38 can enter the entrance channel 54. There is, furthermore, arranged at the first side an exit 74 of the restricted guide 50, at which the latching element 38 can exit from the exit channel 64.

A projection 76 is formed on the circulation body 32 between the entrance 72 and the exit 74. The projection 76 has a control surface 78. The control surface 78 has an inclination relative to the direction defined by the coupling element 36. The inclination of the control surface 78 runs in the direction of entry of the coupling element 36 into the entrance channel 54.

The latching receptacle 52 is a latching recess on the side of the projection 76 facing away from the coupling element 36.

The bearing element 48 is arranged at the second side of the circulation body 32. The bearing element 48 defines an axis of rotation 80. The circulation body 32 is pivotable about the axis of rotation 80 on the bearing element 48 relative to the container wall 18.

Owing to the thermally actuatable actuating element 40, in the sterilization container 10 the valve opening 20 can be opened and closed again, starting from the closed position of the valve body 24, by the sterilization container 10 being subjected during the sterilization process to several cycles, namely two, of changes in temperature. The valve opening 20 is opened during heating, remains in the open state during cooling, and only after heating again and subsequent cooling is the valve opening 20 closed again. The circulation detent device 30 is used for this purpose. This will be explained hereinbelow with reference, in particular, to FIGS. 2 to 5.

It is assumed that the valve body 24 assumes the closed state at the start and closes the valve opening 20. The temperature is low, and the actuating element 40 assumes the low-temperature state of lesser extent (first state). The latching element 38 is arranged outside the restricted guide 50 and, for example, positioned opposite the control surface 78. The actuating element 40 and the setting element 68 are of such dimensions that they contact the stop elements 42 and 46 and 46 and 44, respectively. This is shown in FIG. 2.

The actuating element 40 is transferred to the high-temperature state of greater extent (second state) by heating from the lower temperature to a higher temperature. The actuating element 40 expands and is further supported on the stop elements 42 and 46. The stop element 46 and, therefore, the coupling element 36 are displaced relative to the container wall 18. As a result, the valve body 24 is also displaced. The valve body 24 is lifted off the valve opening 20 to open it. Condensate can exit from the container interior 12 through the valve opening 20.

Owing to the actuating element 40 being coupled to the latching element 38, the latching element 38 is also displaced. The latching element 38 contacts the control surface 78, which results in pivoting of the circulation body 32 about the axis of rotation 80. The latching element 38 can enter the entrance channel 54 and slide along the ramp 56. After sliding over the ramp 56, the latching element 38 is positioned in a cul-de-sac-like recess 82 of the entrance channel 54. This is shown in FIG. 3.

The displacement of the stop element 46 occurs with the setting element 68 supported on it undergoing compression.

During cooling, the actuating element 40 can be transferred from the high-temperature state of greater extent to the low-temperature state of lesser extent and be shortened again. As a result, the actuating element 40 is no longer tensioned between the stop elements 42 and 46. The setting element 68 can displace the stop element 46 under pretension and, therefore, the coupling element 36 together with the latching element 38. The latching element 38 contacts the stop member 58 and is guided via the control surface 60 arranged thereon into the latching receptacle 52.

The latching element 38 assumes a latched position in the latching receptacle 52 when the actuating element 40 assumes the first state again. The latching element 38 was, therefore, transferred to the latched position starting from the unlatched position which it assumed when the first state was assumed by the actuating element 40.

The valve body 24 remains lifted off from the valve opening 20 also after cooling and so condensate can continue to be discharged from the container interior 12 through the valve opening 20 (FIG. 4).

Subsequently, upon an increase in temperature again, the actuating element 40 can once again be transferred from the low-temperature state of lesser extent to the high-temperature state of greater extent. As a result, the actuating element 40 again displaces the coupling element 36 and the latching element 38 by being supported on the stop elements 42 and 46. The latching element 38 is lifted up out of the latched position in the latching receptacle 52 and can contact the control surface 62 at the entrance side of the exit channel 64. The circulation body 32 is pivoted about the axis of rotation 80 relative to the container wall 18 and so the latching element 38 is positioned at the start of the exit channel 64.

Upon displacement of the coupling element 36, the setting element 68 is compressed again. The valve body 24 continues to remain lifted off from the valve opening 20 (FIG. 5).

Subsequently, upon a decrease in the temperature, the actuating element 40 can again be transferred from the high-temperature state of greater extent to the low-temperature state of lesser extent. The actuating element 40 no longer lies against both stop elements 42 and 46. The stop element 46 is displaced under the pretensioning action of the setting element 68. As a result, the coupling element 36 and the latching element 38 are also displaced.

The latching element 38 is guided through the exit channel 64. The exit channel 64 has a ramp 84 over which the latching element 38 slides. At the exit side, a stop member 86 is arranged on the ramp 84 in the area of the exit 74. After the latching element 38 exits from the exit channel 64 and, therefore, the restricted guide 50, the stop member 86 ensures that during another change in temperature cycle the latching element 38 will not enter the exit channel 64. For this purpose, it is advantageous for the stop member 86 to be formed as component or extension of the control surface 78.

During displacement of the coupling element 36, the valve body 24 is also moved into the closed position such that the valve opening 20 is sealed. As a result, the valve device 22, in its entirety, is closed.

The last aforementioned cooling procedure is not shown in the drawings. However, at the end of this procedure, the circulation detent device 30 is in a state which has already been explained hereinabove with reference to FIG. 2.

The latching element 38 again assumes the unlatched position. The latching element 38 was transferred to the unlatched position starting from the latched position in the latching receptacle 52 by the actuating element 40 being transferred from the first state to the second state and again to the first state, and by transfer from the second state to the first state, in this case, too, the pretensioning setting element 68 was additionally operative.

Figure 7:
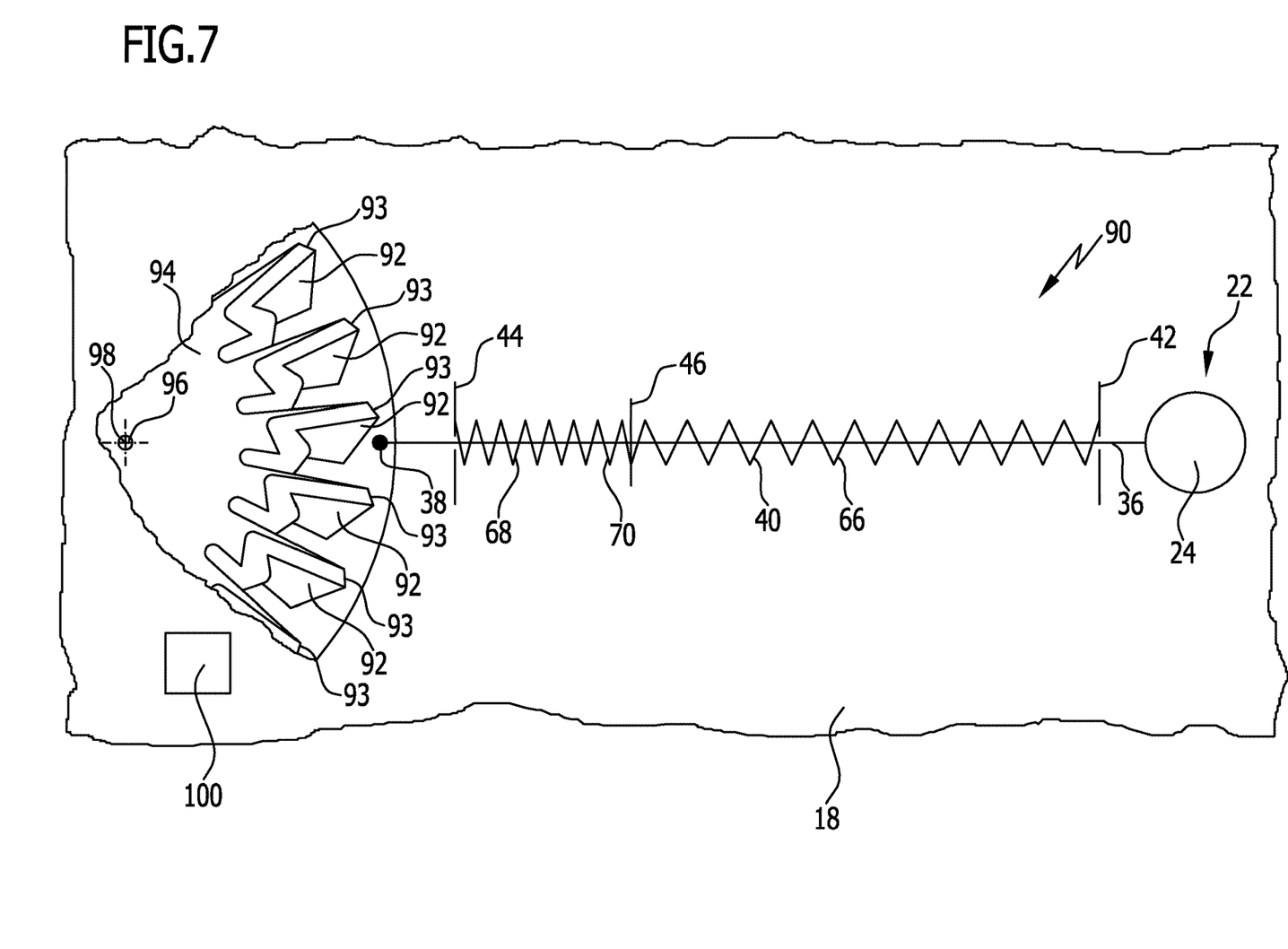
FIG. 7: a schematic partial representation of a further preferred embodiment of a circulation detent device.

FIG. 7 shows in schematic partial representation an advantageous embodiment, denoted by reference numeral 90, of a circulation detent device in accordance with the invention. The same or functionally equivalent features and components of the circulation detent device 30 and 90 are denoted by the same reference numerals. Only the fundamental differences are discussed hereinbelow. The circulation detent device 90 could also be used instead of the circulation detent device 30 in the sterilization container 10.

Instead of only one circulation body 32, a plurality of identical circulation bodies 92 are present in the circulation detent device 90. Functionally, the circulation bodies 32 and 92 are of substantially identical configuration. However, the circulation bodies 92 do not have the bearing element for pivotable bearing on the container wall 18.

Also, instead of the stop member 86, a stop member 93 is provided, which has an inclination which is opposite to that of the control surface 78. This allows the detent element 38, after undergoing two heating and cooling cycles, to be guided to the entrance 72 of the adjacent circulation body 92 prior to the subsequent cycle.

The plurality of circulation bodies 92 are fixed to or formed on a common holding part 94 which comprises a bearing element 96. The bearing element 96 defines an axis of rotation 98 about which the holding part 94 is rotatable on the container wall 18. The circulation bodies 92 are aligned radially in relation to the axis of rotation on the holding part 94 and lie alongside one another.

The circulation bodies 92 are positioned such that there is adjacent to a respective entrance 72 of a restricted guide 50 a respective exit 74 of a restricted guide of an adjacent circulation body 92. After undergoing two heating and cooling cycles with passage through a respective restricted guide 50 of a circulation body 92, the latching element 38 can enter the restricted guide 50 of an adjacent circulation body 92 during the subsequent heating and cooling cycle.

A counter 100 is coupled to the holding part 94. The counter 100 can be of mechanical and/or electrical configuration and, for example, comprise a display with which the number of rotations of the holding part 94 can be counted. With n circulation bodies 92 present on a holding part 94, 2n heating and cooling cycles are required to bring about a rotation of the holding part 94. The number of opening and closing procedures of the valve device 22 can thereby also be counted.

LIST OF REFERENCE NUMERALS 10 sterilization container
12 container interior
14 sterilization container tub
16 sterilization container lid
18 container wall
20 valve opening
22 valve device
24 valve body
30 circulation detent device
32 circulation body
34 operative element 36 coupling element
38 latching element
40 actuating element
42 stop element
44 stop element
46 stop element
48 bearing element
50 restricted guide
52 latching receptacle
54 entrance channel
56 ramp
58 stop member
60 control surface
62 control surface
64 exit channel
66 spring element
68 setting element
70 spring element
72 entrance
74 exit
76 projection
78 control surface
80 axis of rotation
82 recess
84 ramp
86 stop member
90 circulation detent device
92 circulation body
93 stop member
94 holding part
96 bearing element
98 axis of rotation
100 counter

What is claimed is:

1. Medical circulation detent device, comprising:
at least one circulation body,
a latching element, the at least one circulation body comprising a restricted guide and at least one latching receptacle for the latching element, the latching element being guidable through the restricted guide from an unlatched position to a latched position at a first side of the at least one latching receptacle into the latter, and at a second side of the at least one latching receptacle from the latched position to an unlatched position again,
an operative element coupled to the latching element via a coupling element, the operative element comprising a valve body of a valve device, the valve body adapted to close a valve opening of the valve device in a closed position and release the valve opening in an open position, and
a thermal actuating element operatively connected to the latching element and transferable due to temperature from a first state to a second state and vice versa in order to move the operative element, the first state comprises one of a low-temperature state with a lesser extent and a high-temperature state with a greater extent, and the second state comprises the other of the low-temperature state with the lesser extent and the high-temperature state with the greater extent, and wherein:
in order to transfer the latching element from the unlatched position to the latched position in the at least one latching receptacle and in order to transfer the latching element from the latched position to an unlatched position, the thermal actuating element is respectively transferable from the first state to the second state and to the first state again, and the latching element is thereby movable in the restricted guide,
the valve body is transferred from the closed position to the open position and maintained therein by transfer of the latching element from the unlatched position to the latched position, and
the valve body is transferred from the open position to the closed position by transfer of the latching element from the latched position to the unlatched position.

2. Circulation detent device in accordance with claim 1, wherein the first state comprises the low-temperature state with the lesser extent and the second state comprises the high-temperature state with the greater extent.

3. Circulation detent device in accordance with claim 1, wherein the first state comprises the high-temperature state with the greater extent and the second state comprises the low-temperature state with the lesser extent.

4. Circulation detent device in accordance with claim 1, wherein the thermal actuating element consists of or comprises a phase transformation material, which assumes different phase states in the first state and the second state.

5. Circulation detent device in accordance with claim 1, wherein the thermal actuating element consists of or comprises a shape memory material.

6. Circulation detent device in accordance with claim 5, wherein the shape memory material is a two-way shape memory material.

7. Circulation detent device in accordance with claim 5, wherein the shape memory material is nitinol.

8. Circulation detent device in accordance with claim 1, wherein the thermal actuating element is helical and surrounds the coupling element and/or the operative element.

9. Circulation detent device in accordance with claim 1, wherein the circulation detent device comprises or forms at least one stop element, which is fixed to the coupling element, for the thermal actuating element.

10. Circulation detent device in accordance with claim 1, wherein the circulation detent device comprises a setting element which is operatively connected to the latching element and moves the latching element when the thermal actuating element is transferred from the state of greater extent to the state of lesser extent, wherein the setting element is configured as spring element.

11. Circulation detent device in accordance with claim 10, wherein the circulation detent device comprises or forms at least one stop element, which is fixed to the coupling element, for the setting element.

12. Circulation detent device in accordance with claim 1, wherein the coupling element is formed in one piece with the latching element and/or with the operative element.

13. Circulation detent device in accordance with claim 1, wherein the restricted guide is a link guide.

14. Circulation detent device in accordance with claim 1, wherein the at least one latching receptacle is formed as latching recess on the at least one circulation body.

15. Circulation detent device in accordance with claim 1, wherein the restricted guide comprises a ramp for the latching element, over which the latter slides during transfer from the unlatched position to the latched position, and the restricted guide comprises a stop member which holds the latching element back after the sliding-over, and on which a control surface guiding the latching element into the latching receptacle is arranged, wherein the restricted guide comprises an entrance channel, forming the ramp, for the latching element.

16. Circulation detent device in accordance with claim 1, wherein the at least one circulation body comprises precisely one latching receptacle, starting from which the latching element is transferable to the unlatched position.

17. Circulation detent device in accordance with claim 1, wherein the at least one circulation body comprises at least one further latching receptacle for the latching element, in which the latter can assume a further latched position, the thermal actuating element being transferable from the second state to the first state and to the second state again, and the latching element thereby being movable in the restricted guide, in order to transfer the latching element from the latched position to the further latched position.

18. Circulation detent device in accordance with claim 1, wherein the circulation detent device comprises a plurality of circulation bodies fixed or formed on a common holding part, a respective exit of a restricted guide of a circulation body opening into or being adjacent to a respective entrance of a restricted guide of an adjacent circulation body.

19. Medical sterilization container comprising:
- a medical circulation detent device, comprising:
  - at least one circulation body,
  - a latching element, the at least one circulation body comprising a restricted guide and at least one latching receptacle for the latching element, the latching element being guidable through the restricted guide from an unlatched position to a latched position at a first side of the at least one latching receptacle into the latter, and at a second side of the at least one latching receptacle from the latched position to an unlatched position again,
  - an operative element coupled to the latching element via a coupling element, and
  - a thermal actuating element operatively connected to the latching element and transferable due to temperature from a first state to a second state and vice versa in order to move the operative element, the first state comprises one of a low-temperature state with a lesser extent and a high-temperature state with a greater extent, and the second state comprises the other of the low-temperature state with the lesser extent and the high-temperature state with the greater extent, and
  - wherein in order to transfer the latching element from the unlatched position to the latched position in the at least one latching receptacle and in order to transfer the latching element from the latched position to an unlatched position, the thermal actuating element is respectively transferable from the first state to the second state and to the first state again, and the latching element is thereby movable in the restricted guide; and
- a valve device with a valve opening formed in a container wall and a valve body, wherein the valve body comprises the operative element of the circulation detent device, the valve body being transferred from the closed position to the open position and maintained therein by transfer of the latching element from the unlatched position to the latched position, and the valve body being transferred from the open position to the closed position by transfer of the latching element from the latched position to the unlatched position.

* * * * *